(12) United States Patent
Lee et al.

(10) Patent No.: US 6,982,234 B2
(45) Date of Patent: Jan. 3, 2006

(54) METHODS AND APPARATUS FOR REMOVING CATALYST FROM OXIDATION REACTOR EFFLUENT

(75) Inventors: Fu-Ming Lee, Katy, TX (US); Randi Wright Wytcherley, Belgrade, MT (US); Ronald G. Gualy, Houston, TX (US)

(73) Assignee: GTC Technology Inc., Houston, TX (US)

( * ) Notice: Subject to any disclaimer, the term of this patent is extended or adjusted under 35 U.S.C. 154(b) by 0 days.

(21) Appl. No.: 10/309,808

(22) Filed: Dec. 5, 2002

(65) Prior Publication Data

US 2003/0144555 A1   Jul. 31, 2003

Related U.S. Application Data

(63) Continuation-in-part of application No. 09/870,593, filed on Jun. 1, 2001, now abandoned.
(60) Provisional application No. 60/208,666, filed on Jun. 1, 2000.

(51) Int. Cl.
*B01J 20/34* (2006.01)
*C07C 45/00* (2006.01)

(52) U.S. Cl. .......................... 502/22; 502/24; 568/338
(58) Field of Classification Search .................. 502/22, 502/24; 568/338
See application file for complete search history.

(56) References Cited

U.S. PATENT DOCUMENTS 3,959,449 A   5/1976  Shigeyasu et al. .......... 423/488

(Continued)

FOREIGN PATENT DOCUMENTS

| FR | 2 794 991 | 12/2000 |
|---|---|---|
| WO | WO 99/49485 | 12/1997 |
| WO | WO 99/14178 | 3/1999 |
| WO | WO 99/14179 | 3/1999 |
| WO | WO 99/37599 | 7/1999 |
| WO | WO 99/42430 | 8/1999 |

OTHER PUBLICATIONS

International Preliminary Examination Report issued by European Patent Office on Sep. 10, 2002 in PCT application (i.e., PCT/US01/17603) which is related to parent U.S. Appl. No. 09/870,593.

Dr. Jürgen Falbe, et al., Römpp Lexikon Chemie, Georg Thieme Verlag, Stuttgart—New York, pp. 3037–3039, 1998.

Sybil P. Parker, McGraw–Hill Dictionary of Scientific and Technical Terms, Fifth Edition, Washington, D.C., p. 408, 1994.

PCT Written Opinion issued by European Patent Office on Apr. 30, 2002 in PCT application (i.e., PCT/US01/17603) which is related to parent U.S. Appl. No. 09/870,593.

N. Irving Sax and Richard J. Lewis, Sr., Hawley's Condensed Chemical Dictionary, Eleventh Edition, Van Nostrand Reinhold Company Inc., pp. 613–614, 1987.

International Search Report issued by EPO on Dec. 6, 2001 in PCT application (i.e., PCT/US01/17603) which is related to parent U.S. Appl. No. 09/870,593.

*Primary Examiner*—Cecilia J. Tsang
*Assistant Examiner*—Taylor Victor Oh
(74) *Attorney, Agent, or Firm*—Jenkens & Gilchrist, P.C.

(57) ABSTRACT

Methods and apparatus for removing a catalyst from a reaction mixture formed by reacting a hydrocarbon or an oxygenated hydrocarbon with an oxidant in the presence of the catalyst in a reactor, in which the reaction mixture contains one or more dibasic acids. The catalyst is removed by adding water and/or cooling the reaction mixture to cause phase separation, recycling the polar phase to the reactor, and transferring the less-polar phase to an ion exchange unit to remove catalyst contained therein.

11 Claims, 2 Drawing Sheets

U.S. PATENT DOCUMENTS

| | | | |
|---|---|---|---|
| 3,965,164 A | 6/1976 | Blay | 260/531 R |
| 4,162,991 A | 7/1979 | Jones | 252/413 |
| 4,254,283 A | 3/1981 | Mock | 562/530 |
| 5,547,905 A | 8/1996 | Kulsrestha et al. | 502/66 |
| 5,723,098 A | 3/1998 | Salzburg et al. | 423/139 |
| 5,756,837 A | 5/1998 | Costantini et al. | 562/543 |
| 5,840,643 A | 11/1998 | Park et al. | 502/25 |
| 5,880,313 A | 3/1999 | Zaima et al. | 562/414 |
| 5,908,589 A | 6/1999 | DeCoster et al. | 264/37.18 |
| 5,955,394 A | 9/1999 | Kelly | 502/12 |
| 6,039,902 A | 3/2000 | Rostami et al. | 264/37.18 |
| 6,103,933 A | 8/2000 | DeCoster et al. | 562/509 |
| 6,129,875 A | 10/2000 | Dassel et al. | 264/176.1 |
| 6,218,573 B1 | 4/2001 | Vassiliou et al. | 562/543 |

METHODS AND APPARATUS FOR REMOVING CATALYST FROM OXIDATION REACTOR EFFLUENT

This continuation-in-part application claims the benefit of U.S. patent application Ser. No. 09/870,593, filed Jun. 1, 2001, now abandoned, which claims the benefit of U.S. Provisional Application No. 60/208,666, filed Jun. 1, 2000.

BACKGROUND OF THE INVENTION

There are two different types of processes for manufacturing adipic acid. The conventional process for oxidizing cyclohexane (CH) to adipic acid involves two steps: the first step is to oxidize CH with oxygen to produce a mixture of cyclohexanone (CHO) and cyclohexanol (CHOL) at 150° C. in the presence of a cobalt or a manganese catalyst; the second step is to react the mixture of CHO and CHOL with nitric acid to yield adipic acid at 50–80° C. in the presence of a vanadium/copper catalyst. More recently, efforts have been made in the industry to develop a so-called "one-step process" to oxidize CH directly to adipic acid using oxygen in the presence of solvents, catalysts, and promoters.

One such one-step process is disclosed in U.S. Pat. No. 5,547,905 (Kulsrestha, et al.), which involves a catalyst preparation and activation to prepare adipic acid by oxidizing cyclohexane with air or oxygen. The catalyst consists of 70–99 wt % of a cobaltous salt and 1–30 wt % of a ferrous salt and is prepared in the presence of an initiator. The reaction is carried out at a pressure in the range of 1–70 $kg/cm^2$ and a temperature in the range of 70°–150° C., for a period of 1–8 hours at a space velocity of 1–200 $h^{-1}$. The reactor effluent typically contains unreacted cyclohexane, acetic acid (the solvent), water (a reaction product), adipic acid, succinic acid, glutaric acid, and the catalyst.

Recently, some developments have been made in removing and recycling the catalyst (mainly cobalt) from the product streams of such one-step manufacturing processes. The following references may be considered representative: International Publication WO 99/14178 (Rostami, et al.), International Publication WO 99/14179 (Dassel, et al.), International Publication WO 99/37599 (DeCoster, et al.), and International Publication WO 99/42430 (Dassel, et al.). In addition, these applications are related to the following U.S. Patents, which include many of the same inventors: U.S. Pat. No. 5,908,589 (DeCoster, et al.), U.S. Pat. No. 6,039,902 (Rostami, et al.), U.S. Pat. No. 6,103,933 (DeCoster, et al.), U.S. Pat. No. 6,129,875 (Dassel, et al.), and U.S. Pat. No. 6,218,573 (Vassiliou, et al.).

These interrelated documents all disclose methods of recycling a catalyst (cobalt) used in the oxidation of cyclohexane to adipic acid by a one-step process. Before the catalyst is precipitated from the reactor effluent, the major part of the adipic acid and other dibasic acid by-products is recovered, preferably by flash crystallization (under reduced temperature and pressure) followed by filtration.

Catalyst in the filtrate is partially precipitated and removed by reducing the water level in the mixture and/or subjecting the mixture to a temperature at which the catalyst precipitates. After the initial partial precipitation of the catalyst, the remaining mother liquor is subjected to a thermal treatment during which at least the major part of the acetic acid reactor solvent is removed, leaving behind molten dibasic acids, from which additional catalyst is precipitated and removed. The thermal treatment and catalyst removal can be carried out in two stages for better catalyst recovery. However, since the reaction products are recovered before the catalyst is removed, these methods cause the catalyst to co-precipitate or crystallize with the product, which makes the down stream product purification process more complicated and less efficient.

Other patents have discussed various methods for removing catalyst from oxidation reaction mixtures. For example, U.S. Pat. No. 5,880,313 (Zaima, et al.) describes a process in which an aromatic carboxylic acid product is crystallized and removed from the reaction liquid before a catalyst is precipitated. U.S. Pat. No. 5,756,837 (Costantini, et al.) describes a process for recycling a catalyst used in a direct oxidation reaction to convert cyclohexane to adipic acid. The catalyst is recycled by extracting the glutamic and succinic acids that are formed during the reaction. U.S. Pat. No. 4,254,283 (Mock) describes a process for preparing adipic acid from cyclohexanol and cyclohexanone by nitric acid oxidation. Glutamic and succinic acids are recovered as by-products. This process crystallizes the products from the reaction liquid after removing the nitric acid catalyst. Finally, U.S. Pat. No. 4,162,991 (Jones) describes a method for recovering a cobalt and bromide catalyst using a strongly basic anion exchange resin, followed by recovering the ions from the exchange resin by using a lower aliphatic monocarboxylic acid.

U.S. Pat. No. 3,959,449 (Shigayasu, et al.) describes a method for removing catalyst components including cobalt and manganese from a reaction mixture formed when an alkylbenzene is oxidized in a lower aliphatic monocarboxylic acid as a solvent, in the presence of the catalyst. The catalyst is separated by forming an aqueous extract of the catalyst by stirring the reaction mixture with water in the presence of an oxygen-containing gas and a sulfur compound. The extract is then passed through a strongly acidic cation exchange resin to recover the catalyst.

U.S. Pat. No. 5,840,643 (Park, et al.) describes a method for removing a catalyst, including cobalt acetate tetrahydrate and manganese acetate tetrahydrate, from a reaction mixture produced by oxidizing pseudocumene to form trimellitic acid. The catalyst is removed from the reaction mixture before crystallization and distillation processes are performed. The method involves adding water to the reaction mixture in an amount ranging from zero to eleven times the amount of the reaction mixture. The diluted reaction mixture is then heated so that the diluted reaction mixture is in the liquid phase. The mixture is then passed through a cationic exchange resin to recover the catalyst.

U.S. Pat. No. 5,955,394 (Kelly) describes a method for separating a catalyst containing cobalt and manganese from a reaction mixture formed by oxidizing aromatic alkyls to produce aromatic carboxylic acids. The catalyst is removed from the reaction mixture before the reaction product is recovered. The method involves passing the reaction mixture through a strong acid cation exchange resin after heating the mixture to keep the aromatic acids in a dissolved state. The recovered catalyst is recycled to the reactor, and solvent can also be recovered and recycled.

None of the documents discussed above teaches the novel methods and apparatus for removing catalyst from a reaction mixture that are the subject of the present invention. Accordingly, there is a need to develop more efficient methods and apparatus for catalyst removal than those presently known for use in recovering catalysts from oxidation reaction mixtures.

SUMMARY OF THE INVENTION

The present invention provides novel methods and apparatus for effectively removing a catalyst before a reaction product is recovered and purified, which greatly simplifies the purification portion of the recovery process. High purity reaction products may thus be obtained from a reaction mixture obtained by oxidizing cyclohexane in the presence of a catalyst to form adipic acid. Further, reaction efficiency is improved by the ability to recycle the catalyst. Other objects and advantages will be apparent from the detailed description of the invention and the appended claims.

According to a first aspect of our invention, a method for removing a catalyst from a reaction mixture formed by reacting a hydrocarbon or an oxygenated hydrocarbon with an oxidant in the presence of the catalyst includes the steps of cooling and/or adding water to the reaction mixture, separating the reaction mixture into polar and less-polar phases, recycling the polar phase which contains the majority of the catalyst, and removing any remaining catalyst from the less-polar phase using an ion exchange unit. For example, the phase in which water resides or is more abundant is the "polar phase", whereas, the phase lacking water or in which water is less abundant is the "less polar" phase.

According to another aspect of our invention, a method for removing a catalyst from a reaction mixture formed by reacting a hydrocarbon or an oxygenated hydrocarbon with an oxidant in the presence of the catalyst includes the steps of cooling the reaction mixture, and removing catalyst from the reaction mixture using an ion exchange unit.

Yet another aspect of our invention relates to an apparatus for removing a catalyst from a reaction mixture formed by reacting a hydrocarbon or an oxygenated hydrocarbon with an oxidant in the presence of the catalyst in an oxidation reactor. The apparatus includes a phase separator for separating the reaction mixture into polar and less-polar phases, a distillation column for removing excess water from said polar phase and recycling the polar phase which contains the majority of the catalyst back to the reactor, and an ion exchange unit for removing any remaining catalyst from the less-polar phase.

A further aspect of our invention relates to an apparatus for removing a catalyst from a reaction mixture formed by reacting a hydrocarbon or an oxygenated hydrocarbon with an oxidant in the presence of the catalyst in an oxidation reactor. The apparatus includes a unit for cooling the reaction mixture, and ion exchange unit for separating catalyst from the reaction mixture.

These and other aspects of the present invention will become apparent from the following description and the accompanying drawings.

DETAILED DESCRIPTION OF THE PREFERRED EMBODIMENTS

In one-step processes for oxidizing hydrocarbons or oxygenated hydrocarbons at ambient temperature, the reactor effluent can exist where the "solids" (e.g., such as adipic acid) are in solution. The terms reactor effluent and reaction mixtures are used interchangeably throughout this specification. International Publication No. WO 97/49485 and U.S. Pat. No. 6,039,902 report that at this temperature the polar phase (mainly water), is much smaller than the non-polar phase, which makes up roughly 97 volume % of the effluent. However, by adding a small amount of water, about 0.4 to 1 weight %, an appreciable amount of polar phase can be formed, as described, for example, in International Publication No. WO 97/49485, the content of which is herein incorporated by reference in its entirety.

Since both cobalt acetate and ferrous acetate are soluble in water, phase-related adjustments can be made so that substantially all of the metal acetates reside in this polar phase. After phase separation, the polar phase may be processed to recover and recycle the catalyst to the reactor section, while the less-polar phase may optionally be passed through an ion exchange unit or other device to remove the final trace of catalyst before the reaction products are sent on to the product purification section of the process.

We have also found that an ion exchange resin bed is highly effective in removing cobalt from reactor effluent even without using water extraction to pre-reduce the cobalt concentration in the stream. Such a resin bed has been found effective in removing roughly 8,000 ppm cobalt from the reactor effluent. As discussed above, the amount of cobalt in the reactor effluent may be pre-reduced using water extraction before subjecting the effluent to ion exchange treatment if the cobalt levels exceed the ability of the resin to remove the cobalt.

Figure 1:
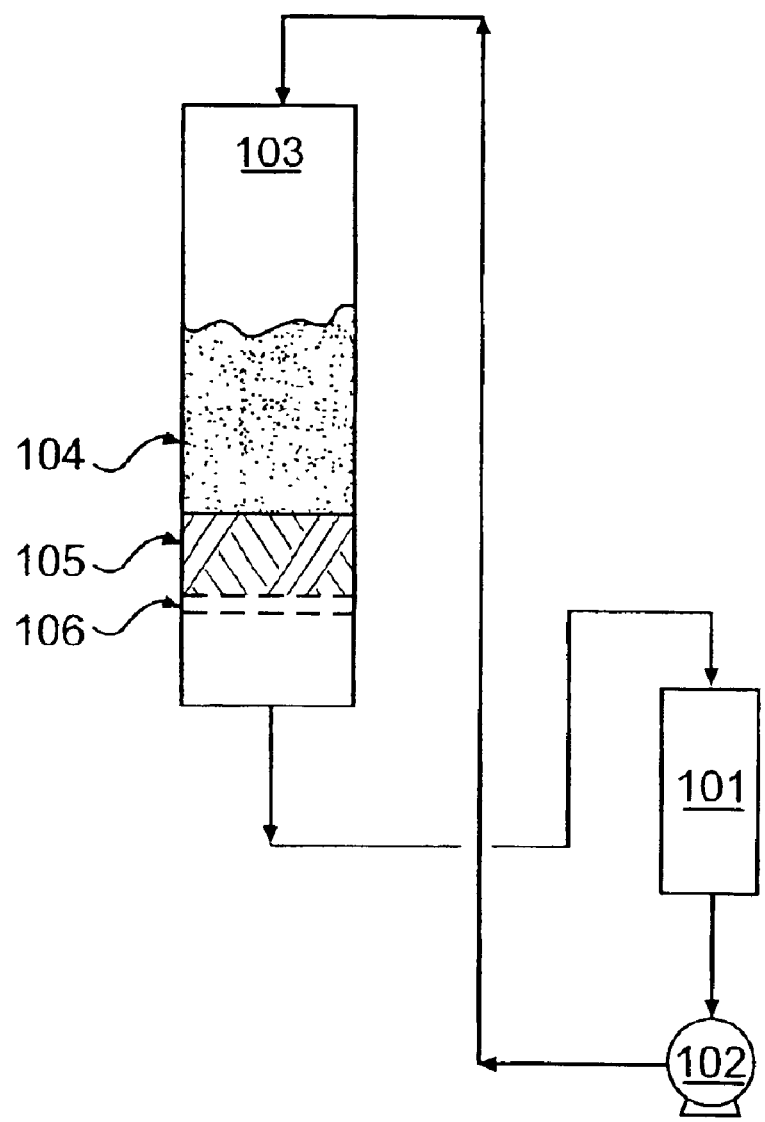
FIG. 1 is an illustration of an ion exchange unit according to the present invention.

FIG. 1 shows an experimental set-up for performing continuous ion exchange on the reactor effluent. The apparatus includes a feed vessel 101 for holding the withdrawn reactor effluent. The feed vessel leads to a pump 102, which withdraws the reactor effluent from the feed vessel 101 and causes it to be introduced into the ion exchange column 103. The ion exchange column 103 is prepared such that the ion exchange resin 104 is packed on top of a quartz layer 105, which is positioned above a frit 106. After the effluent passes through the column 103, it returns to the feed vessel 101. This system allows the effluent to be subjected to continuous ion exchange treatment for optimum removal of catalyst. Although a continuous system for use in a laboratory is shown in FIG. 1, it would be within the knowledge of one skilled in the art to modify this apparatus for use in a system for continuously withdrawing reactor effluent from a one-step oxidation reactor and treating it to remove catalyst contained therein. By removing the catalyst from the effluent, it is possible to recover reaction products of higher purity, thus simplifying the purification process. It is also possible to elute the catalyst trapped in the ion exchange resin, and recover it for further use in the oxidation process.

Figure 2:
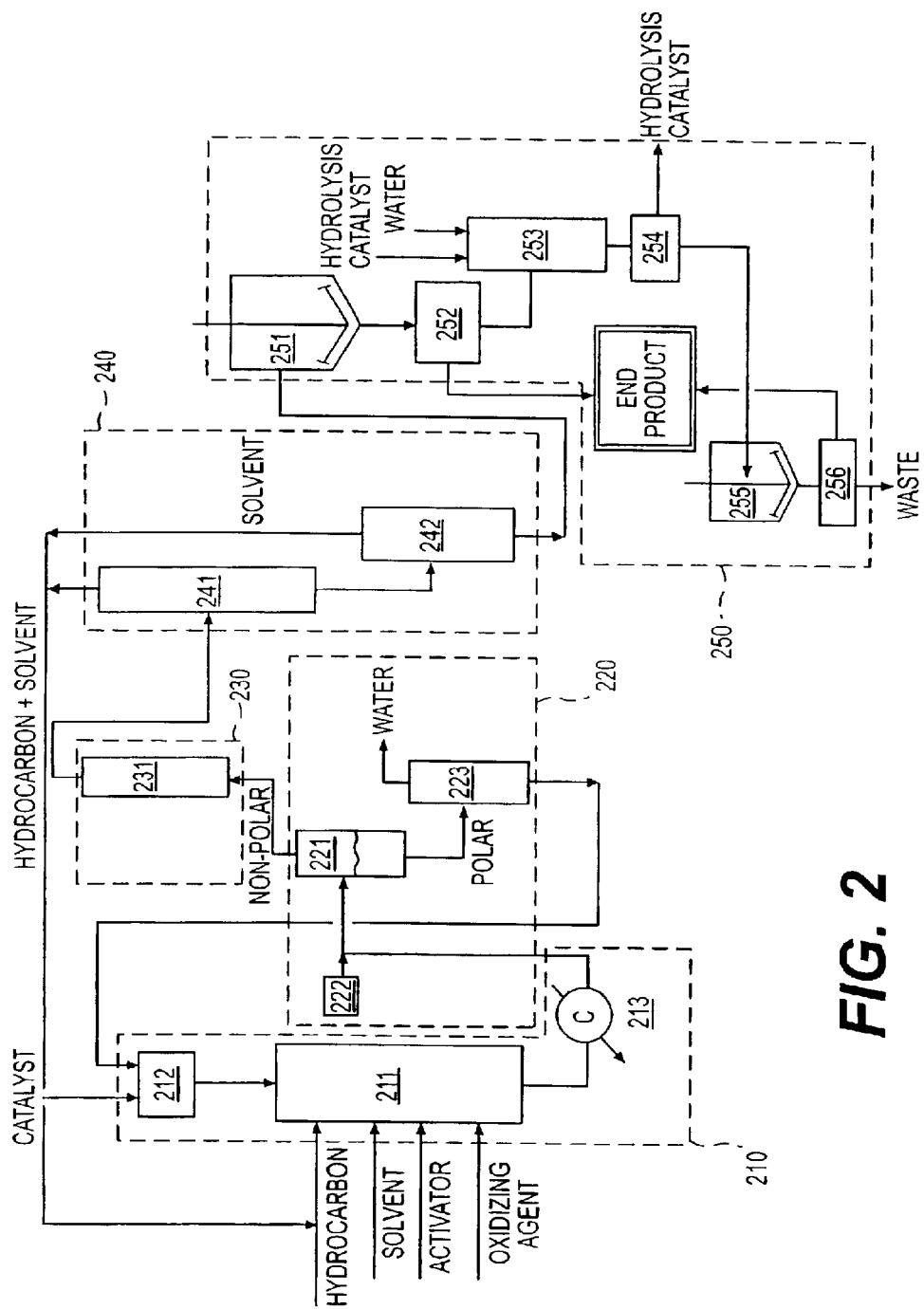
FIG. 2 is a schematic diagram showing a method and apparatus for separating a catalyst from a reaction effluent according to the present invention.

FIG. 2 is a schematic diagram that illustrates a preferred process and apparatus for oxidizing hydrocarbons or oxygenated hydrocarbons to form dibasic acids. This process allows recovery of catalyst from the reactor effluent, with subsequent recycling of the catalyst to the oxidation reactor. The process also allows for purification of the dibasic acid end product, and recycling of the hydrocarbon or the oxygenated hydrocarbon and solvent to the oxidation reactor. The hydrocarbon or oxygenated hydrocarbon may be cyclohexane, cyclohexanone, cyclohexanol, cychlohexylhydroperoxide, or a mixture of two or more of these. A particularly preferred hydrocarbon is cyclohexane. The dibasic acid end product preferably comprises adipic acid, but additional end products may include succinic acid and glutaric acid. The preferred solvent is acetic acid. The catalyst may comprise a cobalt salt, an iron salt, a manganese salt, or it may comprise a mixture of two or more of these salts. This preferred process and apparatus will be discussed in more detail below.

The process according to the preferred embodiment includes several steps: an oxidation step; a phase separation step; an ion exchange step; an optional starting product and solvent recovery step; and an end product recovery and purification step. Each of these steps will be discussed individually for greater clarity.

The oxidation step converts cyclohexane to adipic acid. The reaction is carried out in the presence of a catalyst and oxygen as an oxidizing agent in an acetic acid solvent. The catalyst includes cobalt and iron salts, and a catalyst activator, such as cyclohexanone, may be used. The effluent from the reaction is cooled from the reaction temperature to a temperature that is preferably from about 30° C. to about 100° C., and more preferably from about 30° C. to about 50° C.

The end products and unreacted starting materials contained in the effluent from the oxidation step are subjected to the phase separation step. In this step, water may optionally be added to the effluent before it is separated into its polar and less-polar components. The amount of water added is preferably from about 0 to about 10% by weight of the total reaction mixture, and preferably from about 0.1 to about 5% by weight. The polar phase contains dissolved catalyst, as the cobalt and iron compounds of the catalyst are soluble in water, and a portion of the solvent. This polar phase may be recycled to the oxidation step to catalyze the oxidation reaction. Optionally, water may be removed from the polar phase by incorporating a distillation step before the catalyst is recycled to the oxidation step.

The less-polar phase may also contain small amounts of catalyst, in addition to the adipic acid reaction product, other reaction by-products, unreacted starting materials, and solvent. In order to obtain a high-purity end product without using complicated purification processing, it is desirable to remove substantially all of the catalyst present in the less-polar phase, or as much as is economically feasible. To do so, the less-polar phase is passed through an ion exchange column 231 to remove the catalyst. We have found that this step of the process works well using a highly acidic, cation exchange resin, such as a chelating, methacrylic acid cation exchange resin or a sulfonated polystyrene cation exchange resin. In particular, ResinTech® CG8 (produced by ResinTech, Inc. of Cherry Hill, N.J.) has been found to work extremely well for removing the cobalt and iron catalyst components from the effluent.

Optionally, the less-polar effluent phase may be distilled and evaporated after being passed through the ion exchange column. This step allows unreacted cyclohexane starting material and the acetic acid solvent, both of which are present in the less-polar phase, to be removed and recycled to the oxidation step. Adding this step thereby makes the process more efficient.

The remaining components of the less-polar effluent are subjected to end product recovery and purification, to obtain a high quality adipic acid end product. The recovery and purification is accomplished by crystallizing adipic acid from the effluent, hydrolyzing the liquid remaining after the adipic acid crystals are recovered, and then performing a second crystallization step to recover additional adipic acid. The liquid remaining after the second crystallization step has been performed primarily contains reaction by-products, and is considered waste.

Referring to FIG. 2, the apparatus according to the preferred embodiment includes several units: an oxidation unit 210; a phase separation unit 220; an ion exchange unit 230; an optional recycling unit 240; and a product recovery and purification unit 250. Each unit will be discussed individually for clarity.

The oxidation unit 210 includes the oxidation reactor 211, within which the oxidation of cyclohexane to adipic acid is carried out. The reactor may optionally be associated with a catalyst addition unit 212 and a cooling device 213 for reducing the temperature of the reactor effluent after it exits the reactor.

The phase separation unit 220 includes a phase separator 221, and an optional apparatus 222 for adding water to the reactor effluent. The phase separator separates the reactor effluent into polar and less-polar phases. The polar phase is sent to an optional distillation column 223 for removal of excess water from the polar phase. Catalyst is also found in the polar phase because the catalyst is soluble in water, as discussed above, and therefore, the polar phase is recycled directly to the catalyst addition unit 212 or oxidation reactor 211, where it is used to continue to catalyze the oxidation reaction.

The less-polar phase formed by the phase separator is sent to the ion exchange unit 230 so that any remaining catalyst present in the less-polar phase can be removed. The catalyst is retained in the ion exchange column 231.

The less-polar components of the reactor effluent pass through the ion exchange unit 230 and are optionally sent to a starting product and reaction solvent recycling section 240 before the adipic acid end product is recovered. The starting product and reaction solvent recycling section includes a distillation column 241 and an evaporator 242. The less-polar reactor effluent enters the distillation column 241 after leaving the ion exchange column 231. In the distillation column 241, the cyclohexane starting product and acetic acid solvent are released as the overhead product, and are recycled to the oxidation reactor 211 for use in the oxidation reaction. The column bottoms are optionally sent to an evaporator 242. In the evaporator 242, additional acetic acid is removed and sent to the reactor 211. The remaining less-polar effluent, which includes the desired adipic acid end product as well as other reaction by-products, is sent to the product recovery and purification unit 250.

The product recovery and purification unit 250 includes a first crystallizer 251, a hydrolyzer 253, and a second crystallizer 255. The first crystallizer 251 crystallizes the adipic acid end product from the less-polar reactor effluent. The crystals are present in a slurry, which is then filtered. The crystals retained on the filter 252 are the purified adipic acid end product. The remaining mother liquor may still contain adipic acid, so it is sent to a hydrolyzer 253, which adds water and a hydrolysis catalyst to the liquid to carry out the hydrolyzation. The liquid exiting the hydrolyzer 253 is filtered at filter 254 to recover the hydrolysis catalyst. The filtered liquid is then sent to the second crystallizer 255. The resulting crystalline slurry is filtered, and the crystals retained on the filter 256 are purified adipic acid. The remaining liquid is waste.

The following examples are presented to further illustrate the preferred embodiments of the present invention, and are not intended to limit the scope of the invention.

EXAMPLES

Non-limiting examples 1–3 are provided below. These examples show that an ion exchange resin bed is very effective in removing high amounts of cobalt (roughly 8,000 ppm) from the reactor effluent without using water extraction to pre-reduce the cobalt concentration in the stream. Example 4 demonstrates a process that includes an induced phase separation to pre-reduce the cobalt level in the reactor effluent before it is subjected to ion exchange treatment.

Example 1

This experiment was performed to demonstrate the use of an ion exchange resin to remove cobalt from a reactor product effluent after the unreacted CH and a portion of the acetic acid (HAc) have been removed. The feed mixture has the following composition:

Example 1

| Feed Component | Weight Percent |
| --- | --- |
| Acetic Acid | 86.21 |
| Water | 1.15 |
| Adipic Acid | 8.83 |
| Succinic Acid | 0.56 |
| Cobalt (II) | 0.76 |
| Iron (II) | 0.031 |

The cobalt (II) was cobalt (II) acetate tetrahydrate and the iron (II) was ferrous acetate. The catalyst content in the mixture was not reduced by water extraction before the ion exchange treatment. The feed mixture was mixed with a stirrer at 400 rpm and heated at 60° C. for 30 minutes to dissolve all solids. The resin utilized was Resin Tech® CG8, a high capacity, gelular, sulfonated, polystyrene cation exchange resin.

Resin Preparation

The resin was pretreated to remove the fine resin particles and to obtain the $H^+$ form of the resin. Specifically, the resin was wetted with distilled water by adding enough water to cover the resin by one inch, as measured from the top of the resin bed. Complete mixing was ensured by stirring the wetted resin gently for one minute and allowing the mixture to stand for 15 minutes. The water was decanted, and the wetting process was repeated. The resin was charged by adding a 10 wt % hydrochloric acid (HCl) solution to cover the resin by one inch. The mixture was gently stirred for one minute followed by a contact time of 30 minutes. The 10 wt % HCl was decanted, and the resin was rinsed with 10 bed volumes (the volume of resin initially measured out) of distilled water. The resin was then saturated with cobalt by contacting with an acetic acid solution containing 2 wt % cobalt for 25 hours. The cobalt solution was decanted, and the resin was regenerated. To regenerate, a 10 wt % HCl was added to the resin so that it covered the resin by one inch. The HCl solution contacted the resin for 30 minutes with the aid of magnetic stirring at 200 rpm. The HCl was decanted, and the acid regeneration was repeated. This was followed by four distilled water rinses, with a 5 minute stand time between each rinse.

Cobalt Removal Process

Fourteen grams of regenerated resin were added to a 250 ml container containing 40 grams of feed mixture. The container was stirred at 200 rpm for 6.5 hours to achieve the desired degree of contact. A sample was taken after 6.5 hours and submitted for analysis by inductively coupled plasma spectrophotometry to determine the cobalt concentration present in both the feed mixture and the product stream after contacting them with the ion exchange resin. The results shown below indicate that the ion exchange resin is extremely effective in removing large amounts of cobalt from the reactor effluent.

| Sample | Cobalt (ppm) |
| --- | --- |
| Feed mixture | 7560 |
| Ion exchange Product | 1 |

Example 2

The experiment in Example 1 was repeated using Amberlite® IRC-718, a chelating, methacrylic acid cation exchange resin. The resin preparation procedure and cobalt removal process were the same as those carried out in Example 1. The results shown below indicate that the Amberlite® IRC-718 resin is much less effective than the Resin Tech® CG8 polystyrene cationic exchange resin.

Example 2

| Sample | Cobalt (ppm) |
| --- | --- |
| Feed Mixture | 7560 |
| Ion exchange Produce | 466 |

Example 3

This experiment was performed to remove cobalt from a reconstituted adipic acid reactor effluent, which will be referred to as reconstituted feed, using an ion exchange resin. Again, the catalyst content in the mixture was not reduced by water extraction before the ion exchange treatment. The reconstituted feed consisted of the following:

Example 3

| Reconstituted Feed Component | Weight Percent |
| --- | --- |
| Acetic acid | 76.94 |
| Cyclohexane | 12.40 |
| Water | 1.01 |
| Commercial catalyst solids | 4.87 |
| Commercial crude reactor product | 4.70 |
| Cyclohexanone | 0.042 |
| Cyclohexanol | 0.048 |

The commercial crude reactor product consisted of 98.4 wt % adipic acid and 1.6 wt % cobalt. The commercial catalyst solids consisted of the following components:

| Commercial Catalyst Solids Component | Weight Percent |
| --- | --- |
| Adipic Acid | 31.0 |
| Glutaric Acid | 7.50 |
| Succinic acid | 1.20 |
| Others | 45.03 |
| Cobalt | 15.0 |

The reconstituted feed was mixed with a stirrer and heated at 40° C. for two hours to dissolve all solids. The resin used was Resin Tech® CG8 cation exchange resin.

Resin Preparation

The resin was pretreated to remove fine resin particles and to obtain the $H^+$ form of the resin. Specifically, the resin was wetted with distilled water by adding enough water to cover the resin by one inch. Complete mixing was ensured by stirring the wetted resin gently for one minute and allowing the mixture to stand for 15 minutes. The water was decanted, and the wetting process was repeated. The resin was charged by adding a 10 wt % hydrochloric acid solution to cover the resin by one inch. The mixture was gently stirred for one minute followed by a contact time of 30 minutes. The 10 wt % hydrochloric acid was decanted, and the resin was rinsed with 10 bed volumes (the column resin volume) of distilled water. Lastly, the resin was treated with a 10 bed volume rinse of glacial acetic acid.

Cobalt Removal Process

Five cubic centimeters of resin were added to a #20 two piece column with glass frit (pressure filter funnel), and fifty milliliters of feed were added to a 125 ml Erlenmeyer flask positioned directly below the column.

A feed loop was attached to the column with an in-line pump to produce a feed flow rate of 5 $cm^3$/second through the ion exchange bed. See FIG. 1. The column was operated for 11 hours and 6 minutes to achieve the manufacturer's recommended contact time. Samples were submitted for inductively coupled plasma spectrophotometry analysis to determine the cobalt concentration in both the reconstituted feed and the product stream after contacting them with the ion exchange resin. The results shown below again indicate that the Resin Tech® CG8 cation exchange resin is particularly efficient for removing high amounts of cobalt from a continuous-flow system.

| Sample | Cobalt (ppm) |
| --- | --- |
| Reconstituted Feed | 7967 |
| Ion exchange Product | 2 |

Example 4

Referring to FIG. 2, cyclohexane (CH), acetic acid (HAc), catalyst activator (such as cyclohexanone (CHO)), the catalyst, and oxygen (or air) were fed to a continuous reactor at a predetermined rate of flow. The reactions were carried out at a pressure in the range of 1–70 kg/$cm^2$ and a temperature in the range of 70°–150° C., for a period of 1–8 hours at a space velocity of 1–200 $h^{-1}$. The reactor effluent consisted of unreacted CH, HAc, the catalyst, adipic acid (AA), succinic acid (SA), glutaric acid (GA), MCHA, water, and other minor components.

The reactor effluent was cooled to a desired temperature range and a small amount of water was added to the stream before the stream was introduced to a phase separator. The water addition, although small, causes the polar phase to expand significantly, thus providing better interfacial control in the phase separator. The conditions in the phase separator allow substantially all of the catalyst to reside in the bottom polar phase, with minimal amounts of carboxylic acids present in the polar phase. The polar phase was sent to a distillation column or a flash column to remove water before it was recycled to the reactor section.

The less-polar phase was cooled to a proper temperature before it was fed to an ion exchange column to remove the final trace amount of catalyst. The catalyst-free, less-polar phase was then introduced to a distillation column to remove CH and a portion of the HAc from the column overhead product for recycling to the reactor section. The column bottom stream was transferred to an evaporator to remove additional HAc and to allow purified adipic acid crystals to precipitate in a crystallizer. The slurry from this crystallizer was fed to a filter to recover the purified adipic acid, and the mother liquor was transferred to a hydrolyzer to convert MCHA to adipic acid, where proper amounts of hydrolysis catalyst and water were added to facilitate the reaction. After the hydrolysis catalyst was removed using a filter, additional adipic acid was recovered using a crystallization/filtration step.

While the present invention has been described by what are at present considered the preferred embodiments, the invention is not so limited. On the contrary, the invention is intended to cover various modifications and equivalent arrangements and structures included within the spirit and scope of the appended claims. The scope of the following claims is to be accorded the broadest interpretation so as to encompass all such modifications and equivalent structures and functions.

We claim:

1. A method for removing a catalyst from a reactor effluent formed by reacting a substance that is a cyclical hydrocarbon or a cyclical oxygenated hydrocarbon with an oxidant in the presence of the catalyst in an oxidation reactor, the method comprising the following steps:

cooling the reactor effluent;

separating the reactor effluent into polar and less-polar phases; and transferring the less-polar phase to an ion exchange unit to remove the catalyst, wherein the transferring step is performed prior to recovery of the bulk of any oxidized substance from the reactor effluent, wherein the oxidized substance from the reactor effluent is found in the less-polar phase, and wherein the substance is selected from the group consisting of cyclohexane, cyclohexanone, cyclohexanol, cyclohexylhydroperoxide, and mixtures thereof.

2. The method of claim 1, wherein the oxidant is oxygen or air.

3. The method of claim 1, wherein the catalyst comprises a compound selected from the group consisting of cobalt salt, iron salt, manganese salt, and mixtures thereof.

4. The method of claim 1, wherein the ion exchange unit comprises an ion-exchange resin that is a polymer resin and has cation exchange and acid resistance capability, and is selected from the group consisting of (i) chelating, methacrylic acid cation exchange resins, and (ii) sulfonated, polystyrene cation exchange resins.

5. The method of claim 4, wherein the ion exchange resin is a high capacity, gelular, sulfonated, polystyrene cation exchange resin.

6. The method of claim 1 further comprising a step of:

recycling the polar phase back to the oxidation reactor.

7. The method of claim 6, wherein the reactor effluent is cooled to a temperature in the range of 30°C. to 100°C.

8. The method of claim 7, wherein the reactor effluent is cooled to a temperature in the range of 30°C. to 50°C.

9. The method of claim 6, wherein water is added to the total reactor effluent.

10. The method of claim 9, wherein water is added in the range of from 0.1 weight % to 5 weight % of the total reactor effluent.

11. The method of claim 6, further comprising a step of removing excess water from the polar phase before recycling the polar phase back to the oxidation reactor.

* * * * *

UNITED STATES PATENT AND TRADEMARK OFFICE
CERTIFICATE OF CORRECTION

| | |
|---|---|
| PATENT NO. | : 6,982,234 B2 |
| APPLICATION NO. | : 10/309808 |
| DATED | : January 3, 2006 |
| INVENTOR(S) | : Fu-Ming Lee et al. |

It is certified that error appears in the above-identified patent and that said Letters Patent is hereby corrected as shown below:

Column 4, line 59  Replace "cychlohexylhydroperoxide"
With --cychlohexyl-hydroperoxide--

Signed and Sealed this

Ninth Day of January, 2007

JON W. DUDAS
*Director of the United States Patent and Trademark Office*